United States Patent [19]
Rao

[11] Patent Number: 5,831,136
[45] Date of Patent: Nov. 3, 1998

[54] PROCESS FOR MANUFACTURE OF HIGH PURITY 1,1-DICHLOROTETRAFLUOROETHANE

[75] Inventor: Velliyur Nott Mallikarjuna Rao, Wilmington, Del.

[73] Assignee: E. I. du Pont de Nemours and Company, Wilmington, Del.

[21] Appl. No.: 637,630

[22] PCT Filed: Sep. 1, 1994

[86] PCT No.: PCT/US94/09531

§ 371 Date: Apr. 29, 1996

§ 102(e) Date: Apr. 29, 1996

[87] PCT Pub. No.: WO95/12564

PCT Pub. Date: May 11, 1995

[51] Int. Cl.$^6$ .................................................. C07C 17/00
[52] U.S. Cl. ........................................... 570/168; 570/151
[58] Field of Search .............................................. 570/168

[56] References Cited

U.S. PATENT DOCUMENTS

| | | | |
|---|---|---|---|
| 2,598,411 | 5/1952 | Miller et al. | 260/653 |
| 3,398,202 | 8/1968 | Foulletier. | |
| 3,632,834 | 1/1972 | Christoph | 260/653.7 |
| 4,925,993 | 5/1990 | Zawalski | 570/151 |
| 5,017,732 | 5/1991 | Zawalski | 570/151 |
| 5,055,624 | 10/1991 | Lantz et al. | 570/167 |
| 5,136,113 | 8/1992 | Rao | 570/176 |

FOREIGN PATENT DOCUMENTS

| | | | |
|---|---|---|---|
| 0 317 981 A2 | 5/1989 | European Pat. Off. | C07C 19/08 |
| 0 404 297 | 12/1990 | European Pat. Off. | C07C 17/24 |
| 0 426 343 | 5/1991 | European Pat. Off. | C07C 17/20 |

OTHER PUBLICATIONS

Gervasutti, C. et al., J. Fluorine Chem., 19, 1–20, 1981/82.

Bitner, J.L. et al., U.S. Dept. Comm. Off. Tech. Serv. Rep. 136732, 25–27, 1958.

*Primary Examiner*—Paul J. Killos

[57] ABSTRACT

This invention relates to processes for the manufacturing of 1,1-dichlorotetrafluoroethane (i.e., $CF_3CCl_2F$ or CFC-114a), and more particularly to processes for manufacturing $CF_3CCl_2F$ substantially free of its isomer, 1,2-dichlorotetrafluoroethane (i.e., $CClF_2CClF_2$ or CFC-114).

8 Claims, 1 Drawing Sheet

5,831,136

PROCESS FOR MANUFACTURE OF HIGH PURITY 1,1-DICHLOROTETRAFLUOROETHANE

This application is a national filing under 35 USC 371 of International Application No. PCT/US94/09531 filed Sep. 1, 1994 and claims priority of U.S. patent application Ser. No. 08/146,853 filed Nov. 1, 1993.

BACKGROUND 1,1-Dichlorotetrafluoroethane is of interest as an intermediate to 1,1,1,2-tetrafluoroethane (i.e., $CF_3CH_2F$ or HFC-134a) which can be obtained via catalytic hydrogenolysis of its carbon-chlorine bonds using a supported metal hydrogenation catalyst (see e.g., C. Gervasutti et al., J. Fluorine Chem., 1981/82, 19, pgs. 1–20). HFC-134a is an environmentally acceptable potential replacement for chlorofluorocarbon (i.e., CFC) refrigerants, blowing agents, aerosol propellants and sterilants that are being viewed with concern in connection with the destruction of stratospheric ozone. It is highly desired that the 1,1-dichlorotetrafluoroethane employed in the hydrogenolysis route to HFC-134a has as low a content of 1,2-dichlorotetrafluoroethane as practicable since the presence of CFC-114 during hydrogenolysis can lead to formation of 1,1,2,2-tetrafluoroethane (i.e., $CHF_2CHF_2$ or HFC-134; see e.g., J. L. Bitner et al., U.S. Dep. Comm. Off. Tech. Serv. Rep. 136732, (1958), p. 25). HFC-134 mixed in HFC-134a may be objectionable for some applications depending on concentration and, since the two isomers boil only 7° C. apart, separation of the isomers in high purity is difficult. Commercial processes using either chlorofluorination of $C_2Cl_4$ or fluorination of $C_2Cl_6$ typically yield CFC-114 as the major isomer with CFC-114a as a minor component. Also, the precursor of CFC-114a, 1,1,1-trichlorotrifluoroethane (i.e., $CCl_3CF_3$ or CFC-113a) is typically produced as a minor component when its isomer, 1,1,2-trichlorotrifluoroethane (i.e., $CClF_2CCl_2F$ or CFC-113) is manufactured using similar processes. For example, one well-known and widely-used route to the trichlorotrifluoroethanes and dichlorotetrafluoroethanes involves reaction of hydrogen fluoride (i.e., HF) with tetrachloroethylene (i.e., $C_2Cl_4$) plus chlorine, or with its chlorine addition product, hexachloroethane (i.e., $C_2Cl_6$), in the liquid phase in the presence of an antimony pentahalide as catalyst. The $C_2Cl_3F_3$ and $C_2Cl_2F_4$ products consist predominantly of the more symmetrical isomers, that is, $CClF_2CCl_2F$ and $CClF_2CClF_2$, respectively (the symmetrical term referring to the distribution of the fluorine substituents in the molecule).

Since the boiling points of the two trichlorotrifluoroethanes and of the two dichlorotetrafluoroethanes differ only slightly from one another, separation by conventional distillation on a commercial scale is economically impractical. The lower-boiling dichlorotetrafluoroethanes (boiling range of about 3°–4° C.), however, are readily separable from the trichlorotrifluoroethanes (boiling range of about 46°–48° C.).

U.S. Pat. No. 5,055,624 discloses a process for the selective preparation of CFC-114a by fluorination of pure CFC-113a or mixtures of it with CFC-113 with anhydrous HF. The reaction is done in the liquid phase at 70° to 170° C., under pressure in the presence of an antimony compound of the formula $SbF_xCl_{5-x}$, where x is a number from 1 to 5. In Comparative Example 8, CFC-113 was reacted with HF under a preferred set of conditions at 151° C. to afford a product which contained 99.6 mol % CFC-113 and 0.4 mol % CFC-114. Example 4 discloses the reaction of CFC-113a with HF under similar conditions. A 99.7% yield of CFC-114a of a 61.3% CFC-113a conversion was obtained.

The preparation of the trichlorotrifluoroethanes and the dichlorotetrafluoroethanes by vapor-phase reaction of HF with (A) $C_2Cl_4+Cl_2$ or (B) $CClF_2CCl_2F$ over a suitable catalyst at elevated temperatures has also been well-documented in the art. As disclosed in the art, the vapor-phase processes for $C_2Cl_2F_4$ compounds, whatever the catalyst employed, produce a mixture of the isomers.

European Patent Application No. 317,981-A3 discloses a process for producing $CCl_2FCF_3$ which comprises isomerizing $CCl_2FCClF_2$ to form $CCl_3CF_3$, followed by fluorination with hydrogen fluoride. In the examples, the purest $CCl_2FCF_3$ obtained has a molar ratio of $CCl_2FCF_3$ to $CClF_2CClF_2$ of about 53:1. Also, in the examples the highest purity $CCl_3CF_3$ feed contains about 14% $CCl_2FCClF_2$ and 86% $CCl_3CF_3$.

There remains a need for processes to produce CFC-114a substantially free of its isomer, particularly processes which employ conventional vapor-phase fluorination techniques.

SUMMARY OF THE INVENTION

A process is provided in accordance with this invention for producing $CCl_2FCF_3$ substantially free of $CClF_2CClF_2$. The process comprises the steps of (i) contacting a feed mixture consisting essentially of $C_2Cl_3F_3$ where the ratio of $CCl_2FCClF_2$ to $CCl_3CF_3$ is at least about 1:9 with an isomerization catalyst to produce an isomerization product wherein there is less than about 50,000 parts by weight $CCl_2FCClF_2$ per million parts $CCl_3CF_3$; (ii) contacting the isomerization product with HF in the vapor phase in the presence of a fluorination catalyst comprising trivalent chromium at an elevated temperature below 400° C. selected to provide a fluorination product containing $C_2Cl_2F_4$ and $C_2Cl_3F_3$ wherein there is less than 10,000 parts by weight $CClF_2CClF_2$ per million parts by weight $CCl_2FCF_3$ and wherein the parts by weight $CCl_2FCClF_2$ per million parts $CCl_3CF_3$ is greater than the parts by weight $CCl_2FCClF_2$ per million parts $CCl_3CF_3$ in the isomerization product; (iii) recovering the $C_2Cl_2F_4$ from the fluorination product; and (iv) recycling $C_2Cl_3F_3$ from the fluorination product to step (i) along with an additional amount of $CCl_2FCClF_2$ which is at least equal to the amount of $C_2Cl_2F_4$ recovered in step (iii) and is sufficient to provide said feed mixture ratio of $CCl_2FCClF_2$ to $CCl_3CF_3$.

DETAILED DESCRIPTION

Figure 1:
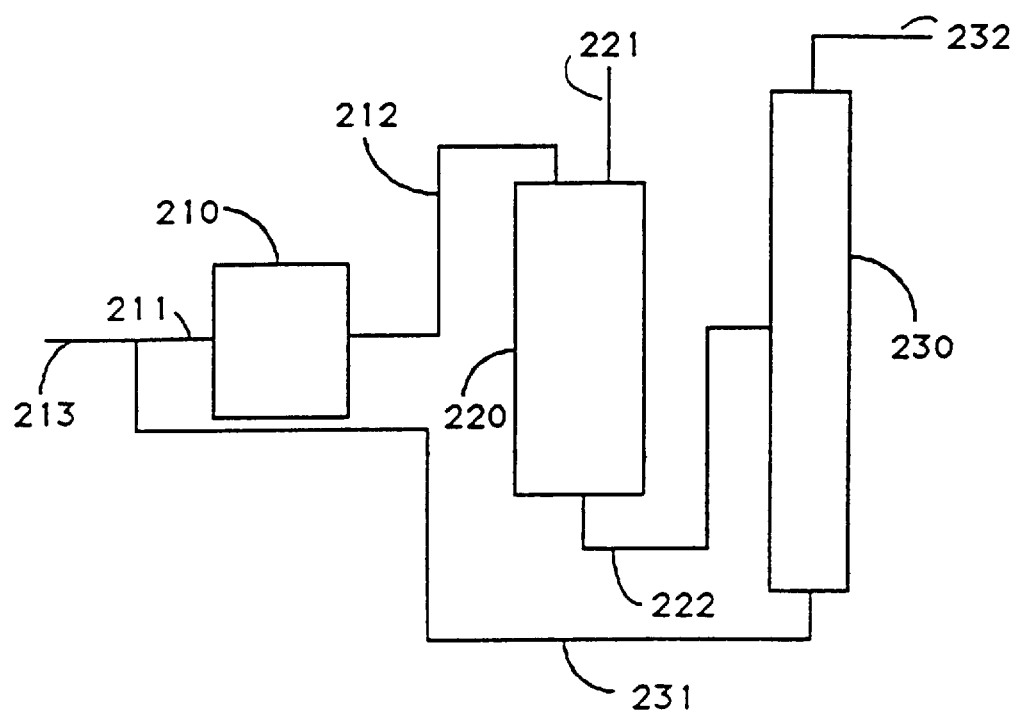
FIG. 1 is a schematic representation of an embodiment of this invention.

The process of this invention involves the vapor phase catalytic fluorination of trichlorotrifluoroethane. $CCl_2FCF_3$ substantially free of $CClF_2CClF_2$ is produced. The $C_2Cl_3F_3$ consists mainly of $CCl_3CF_3$ and less than about 50,000 parts by weight $CCl_2FCClF_2$ per million parts $CCl_3CF_3$. Typically, the $C_2Cl_3F_3$ contains at least about 100 ppm $CCl_2FCClF_2$. For example, $C_2Cl_3F_3$ isomer mixtures recovered from a $CCl_2FCClF_2$ isomerization reaction typically contain from about 300 to 1000 ppm of $CCl_2FCClF_2$ per million parts $CCl_3CF_3$. In accordance with this invention the fluorination is conducted under conditions where $CCl_3CF_3$ is preferentially fluorinated (e.g., at an elevated temperature no higher than about 400° C.). The fluorination process according to the present invention can be conducted batchwise, but is preferably conducted continuously in a manner generally known to the art for conducting catalyzed vapor phase fluorination reactions.

The $C_2Cl_3F_3$ mixtures are reacted with hydrogen fluoride using a catalyst comprising trivalent chromium. In addition to a catalytically effective amount of trivalent chromium, such fluorination catalysts can include other components to increase catalyst activity and/or life such as one or more divalent metal cations (e.g., zinc, magnesium, and/or cobalt). The trivalent chromium catalyst may be unsupported (e.g., $Cr_2O_3$) or supported (e.g., on alumina, aluminum fluoride, magnesium fluoride or carbon).

Suitable vapor-phase fluorination catalysts include trivalent chromium halides (e.g., $CrCl_3$ and/or $CrF_3$) supported on carbon. A preferred catalyst is $CrF_3$ on carbon and is disclosed in U.S. Pat. No. 3,632,834, the contents of which are incorporated herein by reference. While any suitable carbon support may be used, a preferred carbon support is acid-washed prior to depositing trivalent chromium on it. Suitable trivalent chromium catalysts may be prepared by treating the carbon used as catalyst support with an acid, preferably with two acids. Typically the support is washed with deionized water after acid treatment and dried; and the chromium halide is then deposited thereon using deposit techniques well known in the art (see e.g., Example 1 of U.S. Pat. No. 3,632,834). Preferably, the chromium content (expressed as $CrCl_3$) is from about 5 to 50 weight percent of the carbon-supported catalyst.

Acid treatment typically uses an acid other than hydrofluoric acid. Preferred acids used for the acid treatment contain neither phosphorus nor sulfur. Examples of acids which may be used in the first acid wash during the catalyst preparation process include organic acids such as acetic acid and inorganic acids such as HCl or $HNO_3$. Preferably hydrochloric acid or nitric acid is used. The second acid treatment when employed, advantageously uses hydrofluoric acid. Normally, the carbon is treated with acid such that after such treatment the carbon contains less than about 0.1% by weight ash.

Commercially available carbons which may be treated with acids to provide suitable supports include those sold under the following trademarks: Darco™, Nuchar™, Columbia SBV™, Columbia MBV™, Columbia MBQ™, Columbia JXC™, Columbia CXC™, Calgon PCB™, Norit™ and Barnaby Cheny NB™. The carbon support can be in the form of powder, granules, extrudates, or pellets, etc.

The acid treatment may be accomplished in several ways. A suitable procedure is as follows. A carbon support is soaked overnight with gentle stirring in a 1 molar solution of the acid prepared in deionized water. The carbon support is then separated and washed with deionized water until the pH of the washings is about 3. Preferably, the carbon support is then soaked again with gentle stirring in a 1 molar solution of the acid prepared in deionized water for 12 to 24 hours. The carbon support is then finally washed with deionized water until the washings are substantially free of the anion of the acid (e.g., $Cl^-$ or $NO_3^-$), when tested by standard procedures. The carbon support is then separated and dried at about 120° C. The washed carbon is then soaked, if necessary, in 1 molar HF prepared in deionized water for about 48 hours at room temperature with occasional stirring. The carbon support is separated and washed repeatedly with deionized water until the pH of the washings is greater than 4. The carbon support is then dried followed by calcination at about 300° C. for about 3 hours in air prior to its use as a support. Reference is made to U.S. Pat. No. 5,136,113 for further details relating to producing acid-washed carbon catalysts.

For continuous processes, the fluorination reaction is generally conducted in a reaction zone for the fluorination. The reaction zone may contain more than one reactor, multiple feed lines, as well as interstage cooling or heating, addition of reactants, diluents, recycle streams, etc. For example, multiple reactors may be used to stage the degree of fluorination so that undue temperature rise and overfluorination are avoided. The reaction product is normally recovered at the end of the reaction zone. If necessary, the reaction products, intermediates and/or by-products can be removed at various stages of the reaction zone and if desired recycled to different parts of the reaction zone. For example, HF and CFC-113a can be fed to a reaction zone at more than one feed location. CFC-114a is generally recovered from the end of the reaction zone.

Suitable fluorination reaction temperatures are normally from about 250° C. to 400° C. A preferred temperature range is from 275° C. to 375° C., with temperatures ranging from 300° C. to 350° C. being particularly preferred. The $HF:C_2Cl_3F_3$ ratio is normally from 0.2:1 to 4:1, and preferably ranges from 0.25:1 to 2:1. Pressure is not critical. Atmospheric and superatmospheric pressures (e.g., from about 100 kPa to about 7000 kPa) are the most convenient and are therefore preferred. The above reaction variables together with the catalyst loading are balanced one against the other such that in the fluorination products there is less than 10,000 parts by weight $CClF_2CClF_2$ per million parts $CCl_2FCF_3$. One skilled in the art will recognize that higher temperatures and higher $HF:C_2Cl_3F_3$ ratios favor a higher degree of fluorination. The amount of overfluorination can thus be reduced by providing a lower $HF:C_2Cl_3F_3$ ratio and/or lower temperature. Catalyst contact time can also be adjusted in a conventional manner to control fluorination.

In addition to the $C_2Cl_2F_4$ isomers, the fluorination product mixture also typically contains small amounts of $CClF_2CF_3$ (CFC-115), unreacted $C_2Cl_3F_3$ isomers, HF and HCl. The fluorination product is separated to provide recovery of $C_2Cl_2F_4$. Typically, conventional separation using one or more distillation column(s) is employed. It is noted that azeotropes of HF with various halocarbons such as CFC-114a and/or CFC-113a can form during distillation. The separation may also include one or more decanter(s). During separation by distillation, the lower boiling materials (e.g., HF, HCl, CFC-115) are normally separated from the CFC-113 isomers. Normally, the product mixture (prior to recovery of $CCl_2FCF_3$) contains at least 10 mole % $CCl_2FCF_3$ (CFC-114a).

The CFC-113 isomers from the fluorination product, which are normally enriched in CFC-113 as a result of selective fluorination of CFC-113a, are fed along with additional CFC-113 to an isomerization zone, where the CFC-113 is substantially isomerized to CFC-113a. HF should be removed from the $C_2Cl_3F_4$ prior to contact with the isomerization catalyst. The CFC-113 is isomerized to CFC-113a using an aluminum chloride catalyst as disclosed in Example I of U.S. Pat. No. 2,598,411. Many aluminum trihalide catalysts can be employed. A preferred catalyst is an anhydrous aluminum trichloride which has been micropulverized (i.e., mechanically comminuted by crushing, ball milling, rod milling, grinding or the like) to provide a surface area of greater than about 0.8 $m^2/g$ and has been activated by treatment under agitation with at least about 10 grams $CCl_2FCCFl_2$ per gram of aluminum trichloride. Reference is made to copending U.S. patent application Ser. No.

08/117,379 for further discussion of such isomerization. The CFC-113a from the isomerization may be recycled in accordance with this invention to the fluorination step.

The CFC-113a from the isomerization zone is reacted with HF in the reaction zone to afford high purity CFC-114a. The latter compound, which can be isolated from the fluorination product or can be recovered as an azeotrope in the presence of HF, can then be converted by hydrogenolysis to $CH_2FCF_3$ (HFC-134a), a non-ozone depleting refrigerant.

Employment of the instant invention is further illustrated by reference to FIG. 1 wherein a mixture of $C_2Cl_3F_3$ isomers containing substantial CFC-113 is fed through line (211) to an isomerizer (210). The isomerizer effluent consisting of a mixture of $C_2Cl_3F_3$ isomers containing predominantly CFC-113a is fed through line (212) to a fluorination reactor (220). HF is fed to reactor (220) through line (221). The fluorination reactor effluent containing predominantly CFC-114a, unreacted $C_2Cl_3F_3$ isomers, HF and HCl is fed through line (222) to a distillation column (230). $C_2Cl_2F_4$ (CFC-114a substantially free of CFC-114), HF and HCl is collected at the top of the column and recovered through line (232). A mixture of $C_2Cl_3F_3$ isomers enriched in CFC-113, from the bottom of column (230), is fed through line (231) back to the isomerizer (210) along with additional CFC-113 through line (213).

The reactors and their associated feed lines, effluent lines and associated units should be constructed of materials resistant to hydrogen fluoride, hydrogen chloride and chlorine. Typical materials of construction, well-known to the fluorination art, include stainless steels, in particular of the austenitic type, and the well-known high nickel alloys, such as Monel® nickel-copper alloys, Hastelloy® nickel-based alloys and, Inconel® nickel-chromium alloys. Also suitable for reactor fabrication are such polymeric plastics as polytrifluorochloroethylene and polytetrafluoroethylene, generally used as linings.

Practice of the invention will become further apparent from the following non-limiting examples.

EXAMPLES

General Reaction Procedure

A ⅝" (1.58 cm) I.D. Inconel® nickel alloy reactor was charged with a catalyst and heated to 300° C. in a flow of nitrogen (25 mL/min) for about 20 hours. The temperature was reduced to 175° C. and a 2:1 molar ratio of nitrogen to HF was started through the reactor (total flow 100 mL/min). After one hour under these conditions, the molar ratio of nitrogen to HF was adjusted to 1:3 and the temperature increased gradually over a two hour period to 400° C. The reactor was then brought to the desired operating temperature, the nitrogen flow stopped, and the flow of reactants started.

General Analytical Procedure

The reactor effluent was sampled on-line with a Hewlett Packard HP 5890 gas chromatograph using a 20 foot (6.1 m) long, one-eighth inch (0.32 cm) diameter, column containing Krytox™ perfluorinated polyether on an inert support and a helium flow of 35 mL/min. Gas chromatographic conditions were 70° C. for three minutes followed by temperature programming to 180° C. at a rate of 6° C./minute. The table percentages are in mole percent.

Example 1

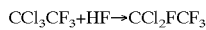

The General Reaction Procedure was followed using a 29% $CrCl_3$ on 4×10 mesh (4.7 mm×1.7 mm) carbon catalyst (12.9 g, 30 mL), a CFC-113a feed containing 99.6% $CCl_3CF_3$ and 0.07% $CCl_2FCClF_2$, an HF:CFC-113a molar ratio of 2:1, a contact time of 30 seconds for the 3 to 90 hr and 100 to 114 hr. samples, a contact time of 15 seconds for the 94 and 98 hour samples and a reaction temperature of 300° C. for all but the 100 to 114 hour samples which were run at 310° C. The reaction was run at atmospheric pressure. The results are shown in Table 1.

TABLE 1

| Time (Hours) | 115[a] | 114a[b] | 113[c] | 113a[d] |
|---|---|---|---|---|
| 3 | 0.2 | 63.7 | 0.04 | 35.5 |
| 21 | 0.1 | 61.4 | 0.03 | 38.3 |
| 30 | 0.1 | 58.4 | 0.03 | 41.4 |
| 48 | 0.1 | 57.9 | 0.03 | 41.9 |
| 78 | 0.1 | 54.4 | 0.03 | 45.4 |
| 94 | 0.1 | 32.7 | 0.03 | 67.2 |
| 114 | 0.2 | 67.6 | 0.03 | 32.1 |

[a] 115 is $CClF_2CF_3$
[b] 114a is $CCl_2FCF_3$
[c] 113 is $CCl_2FCClF_2$
[d] 113a is $CCl_3CF_3$

Selected samples were carefully analyzed on another gas chromatograph to determine the $CClF_2CClF_2$ (CFC-114) content. The 21, 48, 94 and 114 hour samples all had a CFC-114 content below 500 ppm.

Example 2

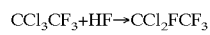

The General Reaction Procedure was followed using 29% $CrCl_3$ on carbon catalyst (9.2 g, 25 mL), a CFC-113a feed containing 98.48% $CCl_3CF_3$, 0.07% $CCl_2FCClF_2$ and 1.21% $CCl_2FCF_3$, an HF:CFC-113a molar ratio of 2:1, a contact time of 30 seconds and a reaction temperature of 300° C. The reaction was run at atmospheric pressure. The results are shown in Table 2.

TABLE 2

| Time (Hours) | 115 | 114a | 113 | 113a |
|---|---|---|---|---|
| 1 | 0.5 | 84.1 | 0.2 | 14.1 |
| 19 | 0.4 | 85.4 | 0.3 | 13.8 |
| 60 | 0.3 | 81.0 | 0.2 | 18.4 |
| 120 | 0.2 | 72.8 | 0.2 | 26.7 |
| 201 | 0.1 | 65.2 | 0.3 | 34.4 |
| 261 | 0.1 | 62.6 | 0.3 | 37.0 |

The CFC-114 was below the detection limit of about 1000 ppm.

Example 3

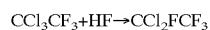

The General Reaction Procedure was followed using 7.5% $CrCl_3$ on carbon catalyst (10.7 g, 30 mL), a CFC-113a feed containing 99.12% $CCl_3CF_3$, 0.25% $CCl_2FCClF_2$, 0.02% $CHCl_2CF_3$ and 0.59% $CCl_2FCF_3$, an HF:CFC-113a molar ratio of 2:1, a contact time of 30 seconds and reaction temperatures as shown in Table 3. The reaction was run at atmospheric pressure. The results are shown in Table 3.

TABLE 3

| Temp. (°C.) | Time (Hours) | 123[a] | 114a | 113 | 113a |
|---|---|---|---|---|---|
| 300 | 1 | 2.8 | 16.9 | 0.3 | 80.0 |
| 300 | 21 | 0.3 | 14.1 | 0.3 | 85.3 |
| 325 | 23 | 0.4 | 36.3 | 0.3 | 62.9 |
| 325 | 43 | 0.2 | 32.1 | 0.3 | 67.3 |
| 350 | 44 | 0.3 | 56.9 | 0.3 | 42.3 |
| 350 | 48 | 0.3 | 55.2 | 0.3 | 44.0 |

[a] 123 is $CHCl_2CF_3$

The CFC-114 was below the detection limit of about 1000 ppm.

Example 4

$CCl_3CF_3 + HF \rightarrow CCl_2FCF_3$

The General Reaction Procedure was followed using 10×20 mesh (1.65 mm×0.83 mm) chrome oxide (39.0 g, 30 mL). A CFC-113a feed containing 99.02% $CCl_3CF_3$, 0.04% $CCl_2FCClF_2$, and 0.88% $CCl_2FCF_3$ was fed to the reactor with HF:CFC-113a molar ratios, contact times (C.T.s) and reaction temperatures as shown in Table 4. The reaction was run at atmospheric pressure. The results are shown in Table 4.

TABLE 4

| Time (Hours) | Molar Ratio HF/113a | Temp. (°C.) | C.T. (Seconds) | 115 | 114a | 113a |
|---|---|---|---|---|---|---|
| 3 | 0.25/1 | 175 | 30 | 0.0 | 2.4 | 97.6 |
| 4 | 0.25/1 | 185 | 30 | 0.0 | 6.2 | 93.7 |
| 5 | 0.25/1 | 195 | 30 | 0.0 | 15.8 | 84.2 |
| 20 | 0.25/1 | 205 | 30 | 0.0 | 5.7 | 94.3 |
| 24 | 0.25/1 | 215 | 30 | 0.0 | 12.6 | 87.4 |
| 28 | 0.25/1 | 225 | 30 | 0.0 | 22.3 | 77.7 |
| 40 | 0.25/1 | 235 | 30 | 0.0 | 23.9 | 76.1 |
| 60 | 0.25/1 | 240 | 30 | 0.0 | 23.7 | 76.2 |
| 80 | 0.25/1 | 245 | 30 | 0.2 | 22.1 | 77.3 |
| 140 | 0.25/1 | 245 | 27 | 0.3 | 23.8 | 75.6 |
| 200 | 0.25/1 | 245 | 30 | 0.5 | 27.9 | 71.2 |
| 230 | 0.5/1 | 245 | 30 | 2.1 | 50.9 | 46.8 |
| 270 | 0.5/1 | 245 | 15 | 1.0 | 51.0 | 47.9 |
| 330 | 0.25/1 | 245 | 30 | 0.4 | 27.2 | 72.0 |
| 348 | 0.25/1 | 245 | 15 | 0.2 | 26.9 | 72.7 |

The CFC-114 was below the detection limit of about 1000 ppm.

Example 5

$CCl_3CF_3 + HF \rightarrow CCl_2FCF_3$

The General Reaction Procedure was followed using 7.5% $CrCl_3$ on non acid-washed carbon (12.84 g, 30 mL).

A CFC-113a feed containing 97.55% $CCl_3CF_3$, 0.07% $CCl_2FCClF_2$, and 2.37% $CCl_2FCF_3$ was fed to the reactor with an HF:CFC-113a molar ratio of 2:1, a 30 second contact time and reaction temperatures as shown in Table 5. The reaction was run at atmospheric pressure. The results are shown in Table 5.

TABLE 5

| Time (Hours) | Temp. (°C.) | 115 | 114a | 123 | 113a |
|---|---|---|---|---|---|
| 5 | 360 | 0.1 | 4.8 | 1.2 | 93.8 |
| 21 | 300 | 0.1 | 4.7 | 0.3 | 94.8 |
| 25 | 325 | 0.2 | 8.4 | 0.5 | 90.7 |
| 42 | 325 | 0.2 | 9.4 | 0.4 | 89.9 |

CFC-114 was below the detection limit of about 1000 ppm..

Example 6

$CCl_3CF_3 + HF \rightarrow CCl_2FCF_3$

The General Reaction Procedure was followed using 7.5% $CrCl_3$ on acid-washed carbon (12.84 g, 30 mL).

A CFC-113a feed containing 97.63% $CCl_3CF_3$, 0.09% $CCl_2FCClF_2$, and 1.91% $CCl_2FCF_3$ was fed to the reactor with an HF:CFC-113a molar ratio of 2:1, a 30 second contact time and at 300° C. The reaction was run at atmospheric pressure. The results are shown in Table 6.

TABLE 6

| Time (Hours) | 115 | 114a | 123 | 113a |
|---|---|---|---|---|
| 1 | 0.2 | 46.0 | 4.1 | 49.4 |
| 9 | 0.1 | 42.7 | 0.9 | 56.2 |
| 19 | 0.1 | 41.3 | 0.5 | 57.8 |
| 27 | 0.1 | 40.0 | 0.4 | 59.3 |
| 35 | 0.1 | 40.0 | 0.3 | 59.4 |
| 45 | 0.1 | 39.1 | 0.3 | 60.3 |

CFC-114 was below the detection limit of about 1000 ppm.

Particular embodiments of the invention are illustrated in the Examples. Other embodiments will become apparent to those skilled in the art from a consideration of the specification or practice without departing from the spirit and scope of the novel concepts of this invention. It is further understood that the invention is not confined to the particular formulations and examples herein illustrated, but it embraces such modified forms thereof as come within the scope of the claims which follow.

I claim:

1. A process for producing $CCl_2FCF_3$ substantially free from $CClF_2CClF_2$, comprising the steps of:
   (i) contacting a feed mixture consisting essentially of $C_2Cl_3F_3$ where the ratio of $CCl_2FCClF_2$ to $CCl_3CF_3$ is at least about 1:9 with an isomerization catalyst to produce an isomerization product wherein there is less than about 50,000 parts by weight $CCl_2FCClF_2$ per million parts $CCl_3CF_3$;
   (ii) contacting the isomerization product with HF in the vapor phase in the presence of a fluorination catalyst comprising trivalent chromium at an elevated temperature below 400° C. selected to provide a fluorination product containing $C_2Cl_2F_4$ and $C_2Cl_3F_3$ wherein there is less than 10,000 parts by weight $CClF_2CClF_2$ per million parts by weight $CCl_2FCF_3$ and wherein the parts by weight $CCl_2FCClF_2$ per million parts $CCl_3CF_3$ is greater than the parts by weight $CCl_2FCClF_2$ per million parts $CCl_3CF_3$ in the isomerization product;

(iii) recovering the $C_2Cl_2F_4$ from the fluorination product; and (iv) recycling $C_2Cl_3F_3$ from the fluorination product to step (i) along with an additional amount of $CCl_2FCClF_2$ which is at least equal to the amount of $C_2Cl_2F_4$ recovered in step (iii) and is sufficient to provide said feed mixture ratio of $CCl_2FCClF_2$ to $CCl_3CF_3$.

2. The process of claim 1 wherein the fluorination catalyst comprises trivalent chromium supported on acid-washed carbon.

3. The process of claim 2 wherein the fluorination catalyst is a chromium halide supported on acid-washed carbon.

4. The process of claim 3 wherein the chromium content of the catalyst is from 5 to 50 weight percent expressed as $CrCl_3$.

5. The process of claim 1 wherein the fluorination reaction temperature is at least about 250° C.

6. The process of claim 1 wherein the fluorination reaction temperature is from 275° C. to 375° C.

7. The process of claim 1 wherein the $HF:C_2Cl_3F_3$ ratio for the fluorination step is from 0.2:1 to 4:1.

8. The process of claim 1 wherein the $HF:C_2Cl_3F_3$ ratio for the fluorination step is from 0.25:1 to 2:1.

\* \* \* \* \*